US010332636B2

(12) United States Patent
Yen et al.

(10) Patent No.: US 10,332,636 B2
(45) Date of Patent: Jun. 25, 2019

(54) CORNEAL YOUNG'S MODULUS ALGORITHM AND SYSTEM USING THE SAME

(71) Applicant: National Taiwan University, Taipei (TW)

(72) Inventors: Jia-Yush Yen, Taipei (TW); I-Jong Wang, Taipei (TW); Po-Jen Shih, Kaohsiung (TW); Chun-Ju Huang, Taipei (TW); Tzu-Han Huang, Taoyuan (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 380 days.

(21) Appl. No.: 15/045,835

(22) Filed: Feb. 17, 2016

(65) Prior Publication Data
US 2016/0239634 A1    Aug. 18, 2016

Related U.S. Application Data

(60) Provisional application No. 62/117,336, filed on Feb. 17, 2015.

(51) Int. Cl.
*A61B 3/10*   (2006.01)
*G16H 50/50*  (2018.01)
(Continued)

(52) U.S. Cl.
CPC ........... *G16H 50/50* (2018.01); *A61B 3/1005* (2013.01); *A61B 3/16* (2013.01); *G06F 19/00* (2013.01);
(Continued)

(58) Field of Classification Search
None
See application file for complete search history.

(56) References Cited

U.S. PATENT DOCUMENTS 5,891,131 A * 4/1999 Rajan ............... A61F 9/00804
                                                    606/5
2002/0116056 A1* 8/2002 Kirk ..................... A61F 2/147
                                                    623/5.11
(Continued)

OTHER PUBLICATIONS

D. C. Pye, "Young's Modulus in Normal Corneas and the Effect on Applanation Tonometry" pp. 445-450, Jun. 2008.*
(Continued)

*Primary Examiner* — Kibrom K Gebresilassie
(74) *Attorney, Agent, or Firm* — Muncy, Geissler, Olds & Lowe, P.C.

(57) ABSTRACT

A corneal young's modulus algorithm and system using the same is provided, comprising a tonometer and a computation unit. The computation unit comprises an algorithm for calculating young's modulus. The algorithm comprises: (S1) read at least one parameter measured by a tonometer; (S2) apply the at least one parameter and an initial value of Young's modulus to a first equation to obtain an inner deformation amount and an outer deformation amount; (S3) apply the inner deformation amount and the outer deformation amount to a second equation to obtain a calculated deformation amount; (S4) determine if an error value between the calculated deformation amount and the actual deformation amount is minimal; and (S5) obtain Young's modulus.

5 Claims, 5 Drawing Sheets

(51) Int. Cl.
*A61B 3/16* (2006.01)
*G06F 19/00* (2018.01)
*A61B 3/00* (2006.01)
*A61B 5/00* (2006.01)

(52) U.S. Cl.
CPC .............. *A61B 3/0025* (2013.01); *A61B 3/165* (2013.01); *A61B 5/0013* (2013.01)

(56) References Cited

U.S. PATENT DOCUMENTS

| 2006/0268224 | A1* | 11/2006 | Brent ........................ | G02C 7/02 |
| | | | | 351/159.18 |
| 2011/0184271 | A1* | 7/2011 | Veciana ................... | A61B 3/16 |
| | | | | 600/398 |
| 2011/0237999 | A1* | 9/2011 | Muller ..................... | A61F 9/008 |
| | | | | 604/20 |
| 2016/0275264 | A1* | 9/2016 | Yen .......................... | G06F 17/13 |

OTHER PUBLICATIONS

S. L. Keeling, G. Propst, G. Stadler, W. Wackernagel, A Mathematical Model for the Deformation of the Eyeball by an Elastic Band, pp. 1-19, Jan. 2009.*

* cited by examiner

CORNEAL YOUNG'S MODULUS ALGORITHM AND SYSTEM USING THE SAME

CROSS REFERENCE TO RELATED APPLICATIONS

This application claims priority of U.S. Provisional Application of Application No. 62/117,336, filed on 17 Feb. 2015, under 35 U.S.C. § 119, the entire contents of all of which are hereby incorporated by reference.

BACKGROUND OF THE INVENTION

1. Field of the Invention

The present invention relates to a corneal Young's modulus algorithm and measuring system using the same, more specifically, an instant and non-invasive corneal Young's modulus measuring system.

2. Description of the Prior Art

As technology advances, it also drives the speedy development of computers, televisions, mobile phones and other digital merchandises. The long hours of using eyes on surfing internet, watching TV, operating the mobile phone cause eyes dry, photophobia, tearing, fatigue, and even with conditions that are accompanied with symptoms of headache, dizziness, nausea, shoulder and neck pain, blurred vision. As a result, eye fatigue has become a common civilization disease of people in the modern society.

Overuse of eyes can result in abnormal function of focus adjustment, loss of efficacy in adjusting the focus length precisely, blurred vision, aggravating myopia, xerophthalmia, or eye diseases such as induced glaucoma and retinal lesion.

Therefore, in addition to a timely rest for the eyes, regular examination of the eyes is particularly important. The common examination used is to measure the intra-ocular pressure (IOP). However, to rely on the IOP value only for determining whether the eyes suffer glaucoma disease may lead to misjudgment since some patients with glaucoma disease appear to have normal IOP values. Therefore, Young's modulus can be used as an auxiliary to increase the accuracy of medical judgment. Through analysis of the Young's modulus, glaucoma symptoms can be more accurately identified; whether an operation of myopia is suitable or not can be determined; and the degree to which wearing the Orthokeratology lens is comfortable or not can be defined.

However, there are generally two types of method to measure Young's modulus of the cornea these days. One method is to retrieve the cornea from the bodies donated and perform in vitro measurement on the cornea using a destructive method. Such method is not helpful for the clinical diagnosis. The other method is to use an applanation tonometer for measuring the cornea through an invasive method by making contact with the patient's cornea directly. The latter is difficult to perform and causes certain degrees of uncomfortable feeling to the patients.

SUMMARY OF THE INVENTION

In view of the above problems, in one aspect, the present invention provides a corneal Young's modulus algorithm, comprising: (S1) read at least one parameter measured by a tonometer; (S2) apply the at least one parameter and an initial value of Young's modulus to a first equation to obtain an inner deformation amount $\overline{W_i}$ and an outer deformation amount $\overline{W_o}$; (S3) apply the inner deformation amount $\overline{W_i}$ and the outer deformation amount $\overline{W_o}$ to a second equation to obtain a calculated deformation amount $\Delta$; (S4) determine if an error value between the calculated deformation amount $\Delta$ and the actual deformation amount is minimal; and (S5) obtain Young's modulus.

In this embodiment, wherein the at least one parameter includes at least dented edge angle $\alpha$, corneal radius R, corneal thickness t, intraocular pressure p, and corneal vertical deformation amount Dt.

In this embodiment, the first equation is $$\left[ \begin{array}{cc} \left\{ \frac{1}{\sqrt{2}} + \frac{2\lambda}{(1-v)} \frac{(1-\cos\alpha)}{\sin\alpha} \right\} & \frac{-1}{\sqrt{2}} \\ \frac{-1}{\sqrt{2}} & \left\{ \frac{3}{\sqrt{2}} + \frac{2\lambda}{1-v}\cot\alpha \right\} \end{array} \right] \left\{ \frac{\overline{W_i}}{\overline{W_o}} \right\} =$$

$$\left\{ \begin{array}{c} -\frac{\alpha}{\lambda} + \frac{\lambda\cot\alpha}{10}\left[\frac{\alpha^2}{\lambda^2} + \frac{1}{2}(\overline{W_o} - \overline{W_i})^2\right] \\ \frac{\alpha}{\lambda} - \frac{\lambda\cot\alpha}{10}\left[\frac{\alpha^2}{\lambda^2} + \frac{1}{2}(\overline{W_o} - \overline{W_i})^2\right] + \frac{t}{\lambda c}\frac{\cos^2\alpha}{\sin\alpha}\overline{p} \end{array} \right\}.$$

In this embodiment, the second equation is $$\frac{\Delta}{R} \equiv (2 + \overline{W_i} - \overline{W_o})(1 - \cos\alpha) - \frac{\lambda}{4\sqrt{2}}\overline{W_o^2}.$$

In this embodiment, wherein if the outcome determined by Step (S4) is "false", return to Step (S2) and follow the optimized procedure to calculate the error value iteratively until the error value is the minimum value.

In another aspect, the present invention provides a corneal Young's modulus measuring system, comprising a tonometer and a computation unit. The tonometer directing an external force to eyes to detect at least one parameter. The computation unit, comprising a corneal Young's modulus algorithm wherein the algorithm includes following steps: (S1) read at least one parameter measured by a tonometer; (S2) apply the at least one parameter and an initial value of Young's modulus to a first equation to obtain an inner deformation amount $\overline{W_i}$ and an outer deformation amount $\overline{W_o}$; (S3) apply the inner deformation amount $\overline{W_i}$ and the outer deformation amount $\overline{W_o}$ to a second equation to obtain a calculated deformation amount $\Delta$; (S4) determine if an error value between the calculated deformation amount $\Delta$ and the actual deformation amount is minimal; and (S5) obtain Young's modulus.

In this embodiment, wherein if the outcome determined by Step (S4) is "false", return to Step (S2) and follow the optimized procedure to calculate the error value iteratively until the error value is the minimum value. Wherein the minimum value is actually 0.

DETAILED DESCRIPTION OF THE PREFERRED EMBODIMENT

Figure 1A:
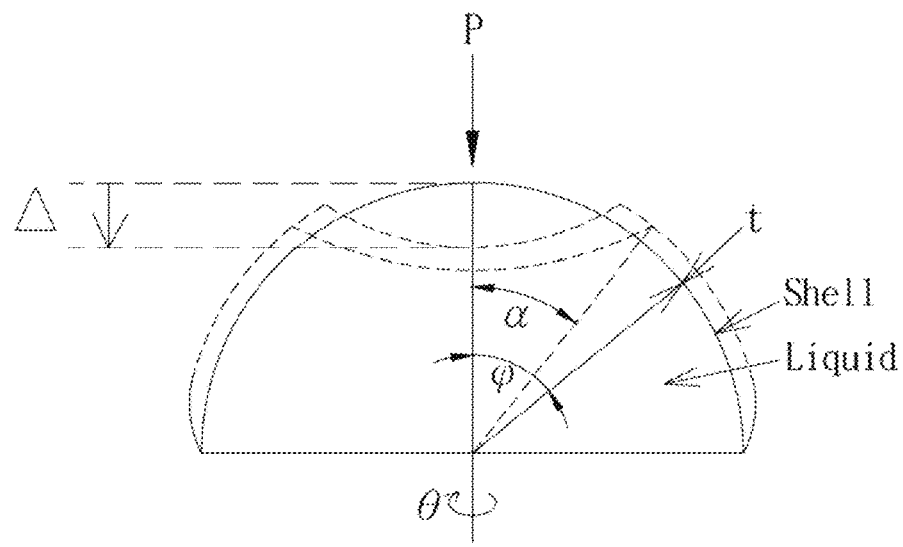
FIG. 1A and FIG. 1B are the schematic diagrams of the force condition of Taber's model.

The following description will be provided along with the diagrams for better understanding of the embodiments of the present invention. For more specific explanations, details of the practical operation will be given as well. However, it should understand that the details on these practical applications do not apply to limit the invention. In addition, to simplify the drawing composition, commonly known structures and elements in the figures are presented by simplified symbols.

A cornea is viewed as a half spherical shell fully filled with fluid in the present invention. The fluid-filled spherical shell model is proposed by Taber describing a fluid-filled incompressible spherical shell model, identical to the anatomical structure of cornea. The present invention relates to the modification and simplification of Taber's model to be applied to the cornea so that the present invention can calculate values of corneal Young's modulus using this static model.

Figure 1B:
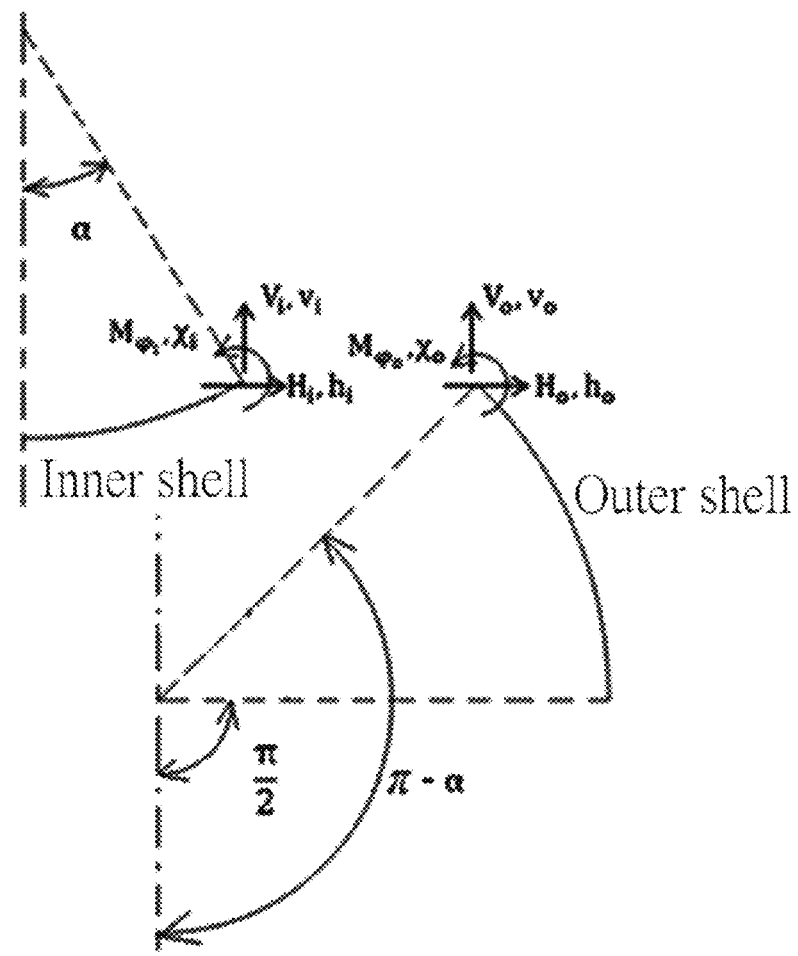

When this model is applied to a cornea, it is under the assumption that the cornea is part of a half spherical shell with its edge fixed already; the spherical shell is composed of homogeneous, isotropic, elastic materials. In addition, load P is directed to the top position of the spherical shell model to cause deformation. The geometric diagrams and the parameter definitions of the spherical shell under force are described in FIG. 1A and FIG. 1B, wherein $M_\phi$ is the meridional moment; H is the horizontal force at the rotation point; X is the rotation angle; h is the horizontal displacement at the rotation point; $\phi$ is the meridional edge angle.

Figures 2A, 2B, 2C:
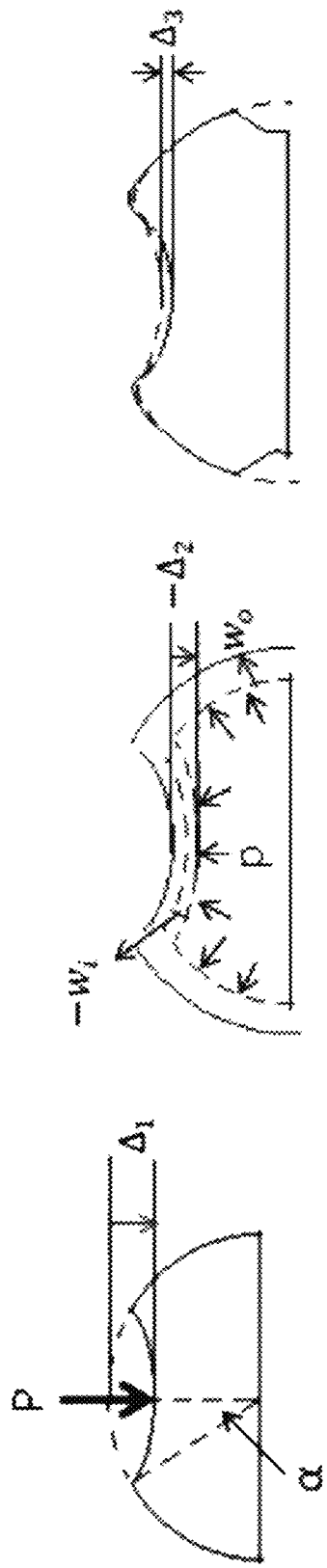
FIG. 2A~ FIG. 2C are the schematic diagrams of Taber's model under force on different portions.

During the process of analyzing the model, we divided the amount of deformation into three parts for investigation in order to derive the needed mathematical equations. Explanations are given as follows. The first part is due to the applied load. The applied load is added to the empty spherical shell and causes an amount of deformation $\Delta_1$. In this case the spherical shell is considered to be an empty spherical shell without any fluid inside and only the impact from the applied load outside the spherical shell to the model is considered. As shown in FIG. 2A, angle $\alpha$ can divide the spherical shell into two parts, that is the inner shell and the outer shell. According to the figure, the amount of deformation $\Delta_1 = 2R(1-\cos\alpha)$ and the equation of volume change of inner shell caused by such deformation amount is $$\Delta V_1 = -\pi R^3 \Delta_1^2 (6 - \Delta_1)/12 \quad \text{(equation 1).}$$

The second part is contributed by stretching. The fluid pressure inside the spherical shell forces the spherical shell to stretch outward. However, due to the impact of the applied load, there are two different radial displacements generated in this part of inner shell and outer shell. Since the outer spherical shell is out the load, the radial displacement of the outer shell can stretch outward without restriction, whereas the radial displacement of the inner shell, which stretches outward, is restricted due to the applied load. As shown in FIG. 2B, after we have normalized two different radial displacements, the values are expressed as inner deformation amount $\overline{w}_i$ and outer deformation amount $\overline{w}_o$ respectively, and also can be viewed to be the amount of deformation before ($\overline{w}_i$) and after ($\overline{w}_o$) the stretch respectively.

In addition, the relationship among meridional strain, the hoop strain and the normalized radial displacements can be expressed as follows:

$$\varepsilon_\phi = \varepsilon_\theta = \begin{cases} \overline{w_i}(\phi^* < \alpha), & \text{innershell} \\ \overline{w_o}(\phi^* > \alpha), & \text{outershell} \end{cases} \quad \text{(equation 2)};$$

the strain energy caused by the internal fluid pressure is:

$$U_s = \frac{\pi E t R^2}{1-v^2} \int (\varepsilon_\phi^2 + \varepsilon_\theta^2 + 2v\varepsilon_\phi\varepsilon_\theta)\sin\phi d\phi, \quad \text{(equation 3)}$$

whereas E is the Young's modulus; t is the thickness of spherical shell; v is the Poisson's radio; $\phi$ is the meridional angle. The meridional angle $\phi$ is determined by the angle position at the outer shell or the inner shell. The strain energy takes into account of both the outward stretch of the outer shell and the downward compression caused by the applied load. Besides, if we substitute the aforementioned (equation 2) into (equation 3), we will have (equation 4) as:

$$U_s = \frac{2\pi E t R^4}{1-v^2}\left[\overline{w_i^2}(1-\cos\alpha) + \overline{w_o^2}\cos\alpha\right].$$

Furthermore, the vertical deformation amount caused by the internal fluid pressure to the spherical shell is expressed by (equation 5):

$$\Delta_2 = R[\overline{w}_i(1-\cos\alpha) - \overline{w}_o \cos\alpha] \quad \text{(equation 5).}$$

The increase in volume change of the inner shell caused by the internal fluid pressure is expressed by (equation 6):

$$\Delta V_2 = -\Delta_2 \int_0^{2\pi}\int_0^\alpha R^2 \sin\phi d\phi d\theta = -2\pi R^3 \Delta_2 (1-\cos\alpha) \quad \text{(equation 6).}$$

The third part is due to impact of bending. For bending force, we have added a restriction to the base edge of the spherical shell, keeping the base areas of the spherical shell before and after deformation are the same. Due to this restriction, unlike what happens the aforementioned second part of force, the spherical shell can not homogeneously expand outward, as a result, so that the spherical shell became bent and further deformed. As show in FIG. 2C, the bending strain energy is expressed by (equation 7):

$$U_B = 2\pi R \sin\phi_e \left[\int_0^X M_\phi d_X + \int_0^h H dh\right] \quad \text{(equation 7).}$$

Next, through the thin-shell model proposed by Ranjan, X and h are used to restrict the edge force $M_\phi$ and H. Once the boundary condition of the edge is taken into account, the bending strain energy can be expressed by (equation 8):

$$U_B = 2\pi E t c^2 \frac{\lambda \sin\alpha}{\alpha} \quad \text{(equation 8)}$$

$$\left\{\sqrt{2}\left[\alpha^3 + \lambda^2\alpha(y_3^2 + y_4^2)\right] + 2\lambda^2\alpha y_3 y_4 - \lambda\alpha^2\Delta\overline{w} + \right.$$

$$\left. \frac{\sqrt{2}\lambda^2\alpha\Delta\overline{w}^2}{4} - \left(\frac{\alpha\cot\alpha}{10}\left[2\sqrt{2}(\alpha^3 + 3\lambda^2\alpha y_3^2) + 4\lambda^2\alpha y_3\right.\right.\right.$$

-continued
$$y_4 - \lambda\alpha^2\Delta\overline{w} - \lambda^3\Delta\overline{w}\left(y_3^2 + 2y_4^2 + \frac{\Delta\overline{w}^2}{6}\right)\right\} +$$

$$\lambda^3\sin\alpha\left[\frac{\sqrt{2}\,\overline{w}_o^2}{2} + \frac{\lambda\cot\alpha\overline{w}_o^3}{15}\right], \text{ whereas}$$

$$\lambda = \sqrt{\frac{R}{c}}, c = \frac{t}{\sqrt{12(1-v^2)}},$$

$$\Delta\overline{w} = (\overline{w}_o - \overline{w}_i).$$

$y_3$ and $y_4$ are the rotation angle displacement and the horizontal displacement respectively. Besides, the deformation amount of the spherical shell by bending in this part is expressed by (equation 9) as:

$$\Delta_3 = R\left\{-2y_4\cos\alpha + \frac{\alpha}{2\sqrt{2}\sin\alpha}\left[2y_3 - \frac{\lambda}{\alpha}y_4(\overline{w}_o - \overline{w}_i)\right] - \frac{\lambda}{4\sqrt{2}}\overline{w}_o^2\right\}.$$ (equation 9)

The volume change of the inner shell due to such deformation is described in (equation 10):

$$\Delta V_3 = -2\pi R^3 \Delta_3 (1-\cos\alpha)$$ (equation 10).

According to aforementioned three parts of discussion, the vertical deformation amount, the volume change of the inner shell due to deformation, the strain energy due to stretching, the strain energy due to bending of the spherical shell caused by each aforementioned part of force can be derived. As for the volume, the volume change of the inner shell will lead to outward expansion of the outer shell so that the volume thereof increases. The relationship of volume change is described by (equation 11) as:

$$\Delta V_4 = 2\pi R^3 \overline{w}_o \cos\alpha$$ (equation 11).

In addition, the energy generated by the work contributed by the applied load P and the internal fluid pressure p on the spherical shell at the same time. The work produced by the applied load P on the spherical shell is expressed by (equation 12) as:

$$U_p = -P(\Delta_1 + \Delta_2 + \Delta_3)$$ (equation 12)

the work produced by the internal fluid pressure p on the spherical shell is expressed by (equation 13) as:

$$U_{pr} = -p(\Delta V_1 + \Delta V_2 + \Delta V_3 + \Delta 4)$$ (equation 13)

In summary of the aforementioned two equations, the total energy generated during the model deformation process of the spherical shell is expressed as $$\Pi = U_s + U_B + U_P + U_{pr}$$ (equation 14)

However, due to the law of conservation of energy, the following equation shall be satisfied:

$$\frac{\partial\Pi}{\partial\overline{w}_i} = \frac{\partial\Pi}{\partial\overline{w}_o} = \frac{\partial\Pi}{\partial\overline{p}} = \frac{\partial\Pi}{\partial y_3} = \frac{\partial\Pi}{\partial y_4} = 0.$$ (equation 15)

Through (equation 15), five non-linear algebraic equations composed of five unknown numbers, $\overline{w}_i$, $\overline{w}_o$, $\overline{p}$, $y_3$ and $y_4$, can be derived, whereas based on (equation 15), the total volume change of the inner shell and the outer shell must be equal to zero. In other words, $(\Delta V_1 + \Delta V_2 + \Delta V_3 + \Delta V_4 = 0)$ and the internal fluid must be incompressible. After (equation 15) is reorganized, the relationship of load and the displacement can be expressed in a matrix form, as shown in (equation 16):

$$A \cdot Z = B_L + B_{NL}$$ (equation 16), whereas vector solution Z is defined as $$Z = \{\overline{w}_i\ \overline{w}_o\ \overline{p}\ y_3\ y_4\}^T$$ (equation 17);

$\overline{w}_i$ and $\overline{w}_o$ are the normalized radial deformation amount of the inner shell and the outer shell respectively; $\overline{p} = pR^2/Et^2$ is the normalized internal fluid pressure of the spherical shell; $y_3$ and $y_4$ are the rotation angle displacement and the horizontal displacement of the spherical shell respectively.

Matrix A is expressed by (equation 18) as:

$$A = \begin{bmatrix} \left\{\frac{1}{\sqrt{2}} + \frac{2\lambda}{(1-v)}\frac{(1-\cos\alpha)}{\sin\alpha}\right\} & \frac{-1}{\sqrt{2}} & \left\{\frac{t}{\lambda c}\frac{(1-\cos\alpha)^2}{\sin\alpha}\right\} & 0 & 0 \\ \frac{-1}{\sqrt{2}} & \left\{\frac{3}{\sqrt{2}} + \frac{2\lambda}{(1-v)}\cot\alpha\right\} & \left\{\frac{-t}{\lambda c}\left(\frac{2-}{\cos\alpha}\right)\cot\alpha\right\} & 0 & 0 \\ -(1-\cos\alpha) & \cos\alpha(2-\cos\alpha) & 0 & 0 & 2\cos\alpha(1-\cos\alpha) \\ 0 & 0 & 0 & \sqrt{2} & 1 \\ 0 & 0 & \left\{\frac{-t}{\lambda c}\left(\frac{1-}{\cos\alpha}\right)\cot\alpha\right\} & 1 & \sqrt{2} \end{bmatrix};$$ (equation 18)

vector $B_L$ is the linear item of (equation 16) and can be described by (equation 19):

$$B = \left\{-\frac{\alpha}{\lambda} + \frac{\overline{P}}{2\pi}\frac{t}{\lambda c}\frac{(1-\cos\alpha)}{\sin\alpha}\ \ \frac{\alpha}{\lambda} - \frac{\overline{P}}{2\pi}\frac{t}{\lambda c}\cot\alpha\ \ (1-\cos\alpha)^2\ \ 0\ \ -\frac{\overline{P}}{2\pi}\frac{t}{\lambda c}\cot\alpha\right\}^T;$$ (equation 19)

vector $B_{NL}$ is the non-linear item in (equation 16) and can be expressed by (equation 20):

$$B_{NL} = \begin{Bmatrix} \frac{\lambda \cot\alpha}{10}\left[\frac{\alpha^2}{\lambda^2} + y_3^2 + 2y_4^2 + \frac{1}{2}\Delta\bar{w}^2\right] + \frac{t}{c}\frac{y_4}{2\sqrt{2}\sin^2\alpha}P^* \\ -\frac{\lambda \cot\alpha}{10}\left[\frac{\alpha^2}{\lambda^2} + y_3^2 + 2y_4^2 + \frac{1}{2}\Delta\bar{w}^2\right] - \frac{t}{c}\frac{y_4}{2\sqrt{2}\sin^2\alpha}P^* - \frac{\bar{P}}{2\pi}\frac{t}{\lambda c}\cot\alpha - \frac{\lambda\cot\alpha}{5}\bar{w}_o^2 \\ \frac{-(1-\cos\alpha)^3}{3} + \frac{\alpha}{2\sqrt{2}}\frac{(1-\cos\alpha)}{\sin\alpha}\left(2y_3 - \frac{\lambda}{\alpha}y_4\Delta\bar{w}\right) \\ \frac{\lambda\cot\alpha}{10}\left(6\sqrt{2}\frac{\alpha}{\lambda}y_3 + 2\frac{\alpha}{\lambda}y_4 - y_3\Delta\bar{w}\right) + \frac{t}{\lambda c}\frac{\alpha P^*}{2\sqrt{2}\sin^2\alpha} \\ \frac{\cot\alpha}{5}(\alpha y_3 - \lambda\Delta\bar{w}y_4) - \frac{t}{c}\frac{\Delta\bar{w}P^*}{4\sqrt{2}\sin^2\alpha} \end{Bmatrix}$$

(equation 20)

In the aforementioned (equation 10) and (equation 20), $\Delta\bar{w} = \bar{w}_o - \bar{w}_i$, $\bar{P} = P/Et^2$ is the normalized applied load;

$$P^* = \frac{\bar{P}}{2\pi} - (1-\cos\alpha)\bar{p}$$

is a mathematic equation composed of a normalized applied load and a normalized internal fluid pressure.

Although, an equation (equation 16) representing the relationship between the load and the displacement can be derived based on the law of conservation of energy, however, in a real situation, not all the conditions can be solved with a convergent solution using (equation 16). For example, when the equation is applied to a thicker spherical shell, a convergent solution can not be obtained. Therefore, to avoid such situation from happening, Taber proposed another a hypothesis to simplify (equation 16), as described in (equation 21):

$$\Delta_2, \Delta_3 \ll \Delta_1$$ (equation 21)

In other words, in the hypothesis, considering the impact on the deformation amount of the spherical shell, generated from both the steering torque to bend the spherical shell and the internal pressure forcing the spherical shell to stretch outward, to be much smaller than that by the impact of the applied load applying directly to the top position of an empty spherical shell, the equation is simplified.

Using such hypothesis, y3 and y4 is viewed as 0. Based on such assumption, vector $B = B_L + B_{NL}$ can be simplified as the following (equation 22):

$$B = B_L + B_{NL} = \begin{bmatrix} -\frac{\alpha}{\lambda} + \frac{\lambda\cot\alpha}{10}\left[\frac{\alpha^2}{\lambda^2} + \frac{1}{2}(\bar{w}_o - \bar{w}_i)^2\right] + \\ \frac{\bar{P}}{2\pi}\frac{t}{\lambda c}\frac{(1-\cos\alpha)}{\sin\alpha} \\ \frac{\alpha}{\lambda} - \frac{\lambda\cot\alpha}{10}\left[\frac{\alpha^2}{\lambda^2} + \frac{1}{2}(\bar{w}_o - \bar{w}_i)^2\right] - \\ \frac{\bar{P}}{\pi}\frac{t}{\lambda c}\cot\alpha - \frac{\lambda\cot\alpha}{5}\bar{w}_o^2 \\ (1-\cos\alpha)^2 - \frac{(1-\cos\alpha)^3}{3} \\ \frac{t}{\lambda c}\frac{\alpha}{2\sqrt{2}\sin^2\alpha}\left[\frac{\bar{P}}{2\pi} - (1-\cos\alpha)\bar{p}\right] \\ -\frac{\bar{P}}{2\pi}\frac{t}{\lambda c}\cot\alpha - \frac{t}{c}\frac{\alpha\Delta\bar{w}P^*}{4\sqrt{2}\sin^2\alpha} \end{bmatrix}$$

(equation 22)

According to (equation 16) and (equation 22), the relationship of $\bar{P}$ and $\bar{p}$ can be obtained as (equation 23):

$$\bar{P} = 2\pi(1-\cos\alpha)\bar{p}$$ (equation 23).

The aforementioned (equation 23) represents when the deformation amount is comparatively small, only one of the two, the applied load and the internal fluid pressure, is obtained, the other can be derived through the equation (relationship). Substitute (equation 23) into (equation 20) to replace $\bar{P}$ and the equation only contains the parameter $\bar{p}$. Afterward, substitute (equation 22) into (equation 16) to replace the original parameters $B_L$ and $B_{NL}$. After the aforementioned processes have been performed, a simplified equation is obtained as the first equation (No. 1 equation) of the present invention:

$$\begin{bmatrix} \left\{\frac{1}{\sqrt{2}} + \frac{2\lambda}{(1-\nu)}\frac{(1-\cos\alpha)}{\sin\alpha}\right\} & \frac{-1}{\sqrt{2}} \\ \frac{-1}{\sqrt{2}} & \left\{\frac{3}{\sqrt{2}} + \frac{2\lambda}{1-\nu}\cot\alpha\right\} \end{bmatrix} \begin{Bmatrix} \bar{w}_i \\ \bar{w}_o \end{Bmatrix} =$$

$$\begin{Bmatrix} -\frac{\alpha}{\lambda} + \frac{\lambda\cot\alpha}{10}\left[\frac{\alpha^2}{\lambda^2} + \frac{1}{2}(\bar{w}_o - \bar{w}_i)^2\right] \\ \frac{\alpha}{\lambda} - \frac{\lambda\cot\alpha}{10}\left[\frac{\alpha^2}{\lambda^2} + \frac{1}{2}(\bar{w}_o - \bar{w}_i)^2\right] + \frac{t}{\lambda c}\frac{\cos^2\alpha}{\sin\alpha}\bar{p} \end{Bmatrix}$$

(No. 1 equation)

When the geometric parameters can be obtained, $\bar{w}_i$ and $\bar{w}_o$ can be calculated.

Furthermore, according to FIG. 2A- FIG. 2C, a mathematic equation related to the vertical deformation amount of the spherical shell can be derived. Thus, the second equation (No. 2 equation) of the present invention is created as:

$$\frac{\Delta}{R} \equiv (2 + \bar{w}_i - \bar{w}_o)(1-\cos\alpha) - \frac{\lambda}{4\sqrt{2}}\bar{w}_o^2.$$ (No. 2 equation)

When the geometric parameters of a fluid-filled spherical shell are available, the relationship of the vertical deformation amount and the internal fluid press of the spherical shell model can be obtained. In addition, when the geometric parameters, internal fluid pressure and the deformation amount of the spherical shell are known, Young's modulus of the spherical shell can be calculated.

Figure 3:
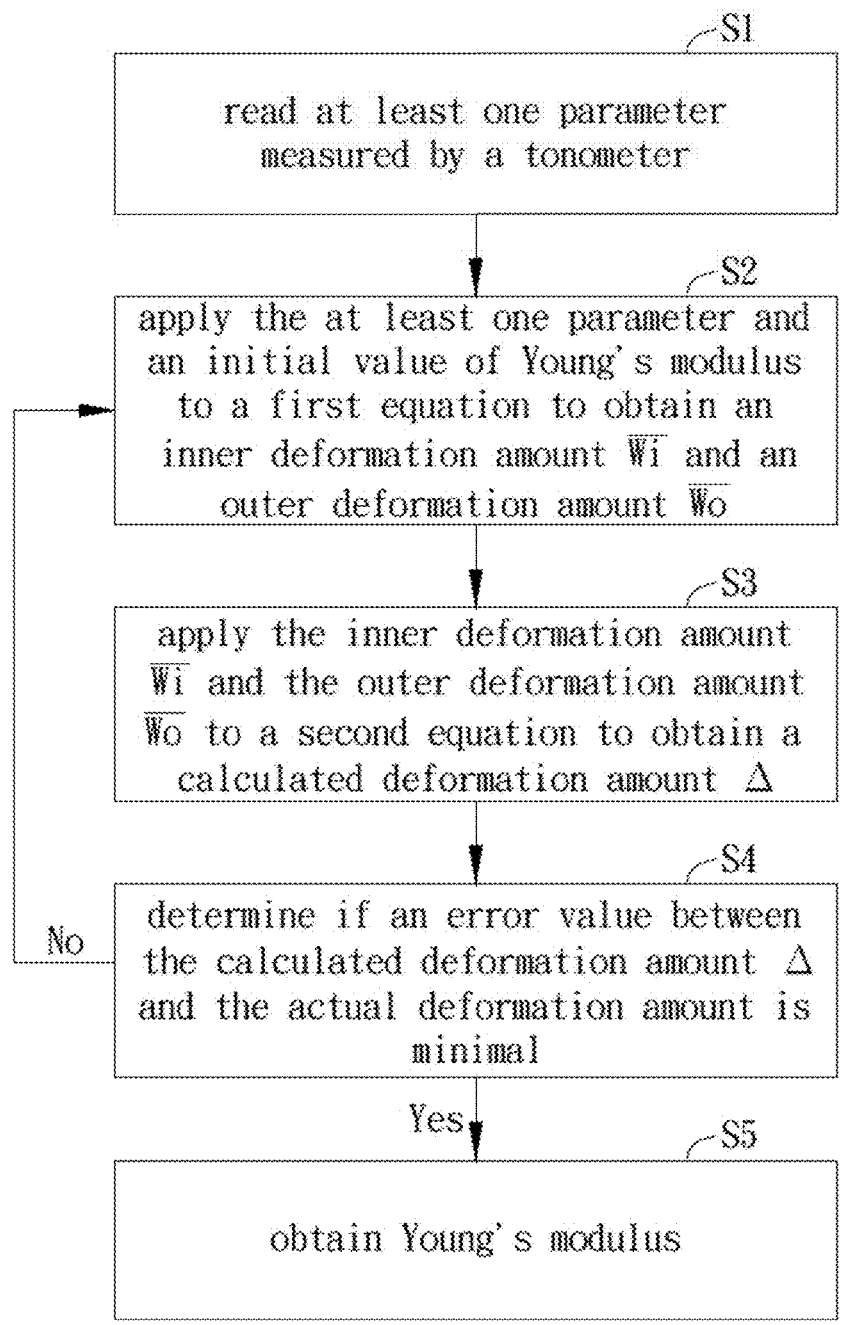
FIG. 3 is the workflow of the embodiment of the Young's modulus calculation method of the cornea of the present invention.

The embodiment of the present invention provides a corneal Young's modulus algorithm, as shown in FIG. 3, comprising the following steps: (S1) read a least one parameter measured by the tonometer; (S2) apply at least one of the parameters and the initial value of Young's modulus to the No. 1 equation to obtain an inner deformation amount $\overline{Wi}$ and an outer deformation amount $\overline{Wo}$; (S3) apply the inner deformation amount $\overline{Wi}$ and the outer deformation amount $\overline{Wo}$ to the No. 2 equation to obtain a calculated deformation amount $\Delta$; (S4) determine if the error value between the calculated deformation amount $\Delta$ and the actual deformation amount is minimal; and (S5) obtain Young's modulus.

Read a least one parameter measured by the tonometer. In other words, through applying external force (applied load) to the eye using a tonometer to obtain relevant parameters. In this embodiment, it is preferable to have parameters including dented edge angle α, corneal radius R, corneal thickness t, intraocular pressure p, and corneal vertical deformation amount Dt.

Figure 4B:
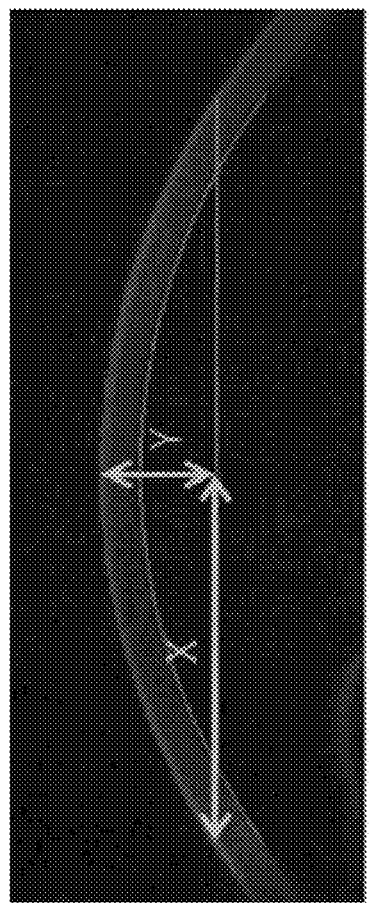
FIG. 4B is the sectional view of the cornea.
Figure 4A:
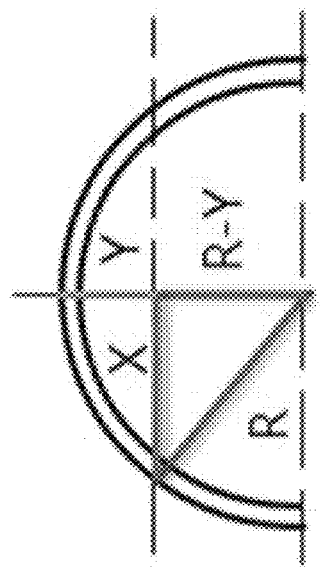
FIG. 4A is the sectional view of the half spherical shell of the Taber's model.

Step (S2): apply at least one of the parameters and the initial value of Young's modulus to the No. 1 equation to obtain an inner deformation amount $\overline{Wi}$ and an outer deformation amount $\overline{Wo}$. In other words, apply the aforementioned parameters α, R, t, p, Dt, and one initial value of Young's modulus to No. 1 equation. In addition, the implicit E in the No. 1 equation is a Young's modulus; v is the Poisson ratio. In this embodiment, the Poisson ratio v is assumed to be, but not limited to, 0.49. In order to apply Taber's model to the eye and to obtain corneal Young's modulus, we view the cornea as part of a half spherical shell, as shown in FIG. 4A. Next, please refer to FIG. 4B, a sectional view of the cornea obtained through an instrument that can be viewed as part of the half spherical shell. According to FIG. 4A and the Pythagorean theorem, the relationship can be established $R^2=X^2+(R-Y)^2$ and it also infers $$R = \frac{X^2 + Y^2}{2Y}.$$

Besides, The present invention only considers the first applanation point (that is the defined point of the IOP) to calculate the corneal Young's modulus. As a result, the needed parameter a for the model can be expressed as $$\alpha = \sin^{-1}\frac{3.06 \times 0.5}{R}$$

wherein the unit of 3.06 is mm, which means when the cornea is pressed by load and reaches the first applanation point, the diameter of the flat area of the cornea created from being pressed by load.

Please note that when these parameters are applied for the first time, an initial value is assumed for Young's modulus. The assumed initial value can be a value based on the past experience or a value provided by the research work. Based on these inputs, the inner deformation amount $\overline{Wi}$ and the outer deformation amount $\overline{Wo}$ can be calculated.

Step (S3): apply the inner deformation amount $\overline{Wi}$ and the outer deformation amount $\overline{Wo}$ to the No. 2 equation to obtain a calculated deformation amount $\Delta$. In other words, $\overline{Wi}$ and $\overline{Wo}$ obtained in the aforementioned step are applied into No. 2 equation to get the calculated deformation amount $\Delta$.

Next, step (S4): determine if the error value between the calculated deformation amount $\Delta$ and the actual deformation amount is minimal. Confirm that the error value between the calculated deformation amount $\Delta$ and the actual deformation amount measured by the tonometer is the minimum value. To confirm there is a minimal error between both value, we used the optimized procedure to calculate iteratively using different Young's moduli in this embodiment in order to obtain the best solution so that the calculated deformation amount $\Delta$ produced by this model can be very closagain e to the actual corneal deformation amount. In this embodiment, the optimized procedure is preferable to be a method of nonlinear programming.

However, when the error value is determined not to be the minimal value, return to step (S2) to calculate iteratively until the error value becomes the minimum value.

It is necessary to explain that in this embodiment, we define the minimal error value to be $10^{-6}$. Actually, the minimum error value can be considered, but not limited to, as 0.

Last, step (S5) is to obtain Young's modulus through the aforementioned steps, that is the optimized solution of Young's modulus.

Further explanation is provided that since the spherical shell model actually is still affected by tension. The tension of a spherical shell can be described in the relation formula $p(\pi R^2) = T(2\pi Rt)$ according to force equilibrium wherein p is the internal pressure of spherical shell, that is the intraocular pressure (IOP); R is the radius of spherical shell; T is the tension; t is the corneal thickness. After re-organizing the relation formula, we get $T = pR / 2t$. At this stage, the unit of T is identical to the pressure unit and also identical to the unit of Young's modulus. In most cases, when the tension unit and the unit of Young's modulus are the same, Young's modulus is equal to the tension.

Figure 5:
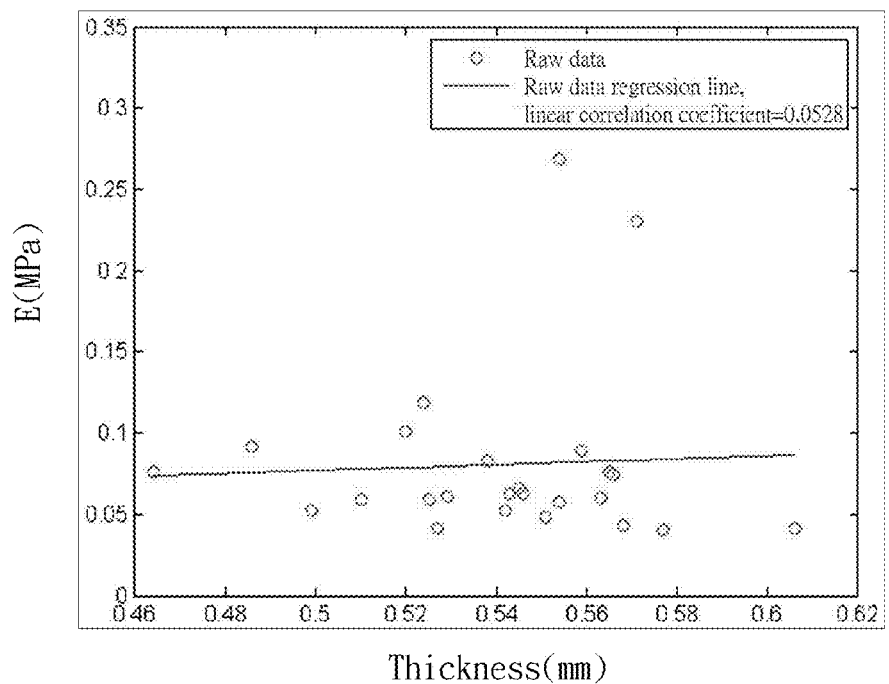
FIG. 5 is a distribution diagram of the correlation between the value of Young's modulus calculated by the present invention and the thickness of cornea.

We conducted the single factor linear regression analysis on the outcomes of Young's modulus and the corneal thickness, as shown in FIG. 5. The Young's moduli by calculation and the corneal thickness have very little corrections in this embodiment and the correlation coefficient between two is only 0.0528. Such outcome meets the fact that Young's modulus is only relevant to materials; in other words, Young's modulus is not affected by the corneal thickness.

Figure 6:
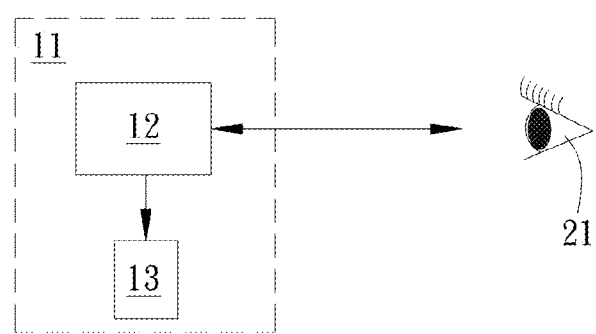
FIG. 6 is the schematic diagram of the embodiment of the corneal Young's modulus measuring system of the present invention.

Another embodiment of the present invention provides a corneal Young's modulus measuring system which mainly applies the aforementioned simplified No. 1 equation and No. 2 equation, along with the use of tonometer to complete the measurement. Explanation is given as follows. As shown in FIG. 6, the corneal Young's modulus measuring system of the present invention, preferably comprising a tonometer 12 and a computation unit 13. The tonometer 12 directs an external force (applied load) to the eye 21 to detect at least one parameter. In the embodiment, the tonometer 12 is, but not limited to, a Corvis ST of Oculus in Germany. Other tonometers can be used in other embodiments. The tonometer uses the high-speed photographic technology to snap 140 corneal sectional images within 31 ms, and calculate and analyze data, including the degree of applanation and rebound when a specific amount of air pressure is blown onto the eye and the speed, in order to evaluate biomechanical characteristics of the cornea.

Using the tonometer 12, parameters obtained preferably include the dented edge angle α, corneal radius R, corneal thickness t, intraocular pressure p, and corneal vertical deformation amount Dt.

The computation unit 13 can be a processor or other members with computing capability. In this embodiment, the aforementioned calculation methods can be stored in the processor for follow-up operation. One thing worth mentioning is that the computation unit 13 in the embodiment can be added onto the tonometer 12 as a hardware setting and connected together externally. However, please note that in other embodiments the computation unit 13 can be stored in the form of firmware or software in the internal circuit of tonometer 12.

In other preferable embodiments, the computation unit can be connected to other devices, for example, computers, for the convenience of performing statistical distributions and analysis for follow-up.

The tonometer 12 transfers the parameters obtained from the measurement to the computation unit 13. After the computation unit 13 retrieves the data, the process begins the calculation according to the calculation method inside, and further produces the Young's modulus, wherein the calculation method is explained in the aforementioned embodiments. No further explanation is provided here.

In comparison to prior art, the present invention can calculate Young's modulus using the corneal Young's modulus algorithm, along with the use of existing tonometer for measurement to instantly measure the corneal Young's modulus.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A corneal stiffness testing method, comprising the following steps:

(S1) read parameters of a corneal through a tonometer, wherein the tonometer snaps corneal sectional images and acquires parameters from the images, and the parameters include dented edge angle α, corneal radius R, corneal thickness t, intraocular pressure p, and corneal vertical deformation $D_t$ of the corneal;

(S2) apply the parameters and an initial value of Young's modulus to a first equation:

$$\begin{bmatrix} \left\{ \frac{1}{\sqrt{2}} + \frac{2\lambda}{(1-v)} \frac{(1-\cos\alpha)}{\sin\alpha} \right\} & \frac{-1}{\sqrt{2}} \\ \frac{-1}{\sqrt{2}} & \left\{ \frac{3}{\sqrt{2}} + \frac{2\lambda}{1-v}\cot\alpha \right\} \end{bmatrix} \begin{Bmatrix} \overline{w_i} \\ \overline{w_o} \end{Bmatrix} = $$

$$\begin{Bmatrix} -\frac{\alpha}{\lambda} + \frac{\lambda\cot\alpha}{10}\left[\frac{\alpha^2}{\lambda^2} + \frac{1}{2}(\overline{w_o} - \overline{w_i})^2\right] \\ \frac{\alpha}{\lambda} - \frac{\lambda\cot\alpha}{10}\left[\frac{\alpha^2}{\lambda^2} + \frac{1}{2}(\overline{w_o} - \overline{w_i})^2\right] + \frac{t}{\lambda c}\frac{\cos^2\alpha}{\sin\alpha}\overline{p} \end{Bmatrix}$$

wherein $$\overline{p} = \frac{pR^2}{Et^2},$$

E is the Young's modulus, v is the Poisson ratio, and obtaining an inner deformation amount $\overline{W_i}$, and an outer deformation amount $\overline{W_o}$;

(S3) apply the inner deformation amount $\overline{W_i}$ and the outer deformation amount $\overline{W_o}$ to a second equation:

$$\frac{\Delta}{R} \equiv (2 + \overline{w_i} - \overline{w_o})(1 - \cos\alpha) - \frac{\lambda}{4\sqrt{2}}\overline{w_o}^2$$

and obtain a calculated deformation amount Δ;

(S4) determine if an error value between the calculated deformation amount Δ and the actual deformation amount $D_t$ is less than or equal to a given minimal value;

(S5) obtain Young's modulus of the corneal through $$\overline{p} = \frac{pR^2}{Et^2};$$

and (S6) determine if the corneal has glaucoma symptoms, myopia, or the requirement to wear Orthokeratology lens with the Young's modulus.

2. The corneal stiffness testing method as claimed in claim 1, wherein if the error value determined by Step (S4) is not less than or equal to the given minimal value, return to Step (S2) and follow an optimized procedure to calculate the error value iteratively until the error value is less than the given minimum value.

3. The corneal stiffness testing method as claimed in claim 1, wherein the error value is equal to the given minimal value when the error value is 0 or approached to 0.

4. A corneal stiffness testing system, comprising:

a tonometer, directing an external force to an eye to detect parameters of corneal of the eye; and a computation unit, computes Young's modulus of the corneal with the parameters, computation unit uses following steps:

(S1) read parameters of a corneal through a tonometer, wherein the tonometer snaps corneal sectional images and acquires parameters from the images, and the parameters include dented edge angle α, corneal radius R, corneal thickness t, intraocular pressure p, and corneal vertical deformation $D_t$ of the corneal;

(S2) apply the parameters and an initial value of Young's modulus to a first equation:

$$\begin{bmatrix} \left\{ \frac{1}{\sqrt{2}} + \frac{2\lambda}{(1-v)} \frac{(1-\cos\alpha)}{\sin\alpha} \right\} & \frac{-1}{\sqrt{2}} \\ \frac{-1}{\sqrt{2}} & \left\{ \frac{3}{\sqrt{2}} + \frac{2\lambda}{1-v}\cot\alpha \right\} \end{bmatrix} \begin{Bmatrix} \overline{w_i} \\ \overline{w_o} \end{Bmatrix} = $$

$$\begin{Bmatrix} -\frac{\alpha}{\lambda} + \frac{\lambda\cot\alpha}{10}\left[\frac{\alpha^2}{\lambda^2} + \frac{1}{2}(\overline{w_o} - \overline{w_i})^2\right] \\ \frac{\alpha}{\lambda} - \frac{\lambda\cot\alpha}{10}\left[\frac{\alpha^2}{\lambda^2} + \frac{1}{2}(\overline{w_o} - \overline{w_i})^2\right] + \frac{t}{\lambda c}\frac{\cos^2\alpha}{\sin\alpha}\overline{p} \end{Bmatrix}$$

wherein $$\bar{p} = \frac{pR^2}{Et^2},$$

is the Young's modulus, v is the Poisson ratio, and obtaining an inner deformation amount $\overline{W_i}$ and an outer deformation amount $\overline{W_o}$;

(S3) apply the inner deformation amount IV, and the outer deformation amount w, to a second equation:

$$\frac{\Delta}{R} \equiv (2 + \overline{w_i} - \overline{w_o})(1 - \cos\alpha) - \frac{\lambda}{4\sqrt{2}} \overline{w_o}^2$$

and obtain a calculated deformation amount $\Delta$;

(S4) determine if an error value between the calculated deformation amount $\Delta$ and the actual deformation amount $D_t$ is less than or equal to a given minimal value;:

(S5) obtain Young's modulus of the corneal through $$\bar{p} = \frac{pR^2}{Et^2};$$

and (S6) determine if the corneal has glaucoma symptoms, myopia, or the requirement to wear Orthokeratology lens with the Young's modulus.

5. The corneal stiffness testing system as claimed in claim 4, wherein if the error value determined by Step (S4) is not less than or equal to the given minimal value, return to Step (S2) and follow an optimized procedure to calculate the error value iteratively until the error value is less than the given minimum value.

* * * * *